United States Patent [19]

Goldman et al.

[11] Patent Number: 4,928,695

[45] Date of Patent: May 29, 1990

[54] LASER DIAGNOSTIC AND TREATMENT DEVICE

[76] Inventors: Leon Goldman, The Devonshire House, 7811 Eads, No. 304, La Jolla, Calif. 92037; Ellet H. Drake, 706 Spring St., Wausau, Wis. 54401; Steven Goldman, 4425 W. Flying Diamond Dr., Tucson, Ariz. 85704

[21] Appl. No.: 312,887

[22] Filed: Feb. 17, 1989

[51] Int. Cl.$^5$ .................. A61N 5/00; A61B 1/06; A61B 17/35
[52] U.S. Cl. .................. 128/642; 128/741; 128/6; 128/786; 606/15
[58] Field of Search .............. 128/633, 634, 665, 642, 128/741, 784, 786, 4, 6; 606/15, 16

[56] References Cited

U.S. PATENT DOCUMENTS

| Re. 32,204 | 7/1986 | Halvorsen . | |
|---|---|---|---|
| 3,313,293 | 4/1967 | Chesebrough et al. . | |
| 3,659,613 | 5/1972 | Bredemeier . | |
| 3,804,095 | 4/1974 | Bredemeier . | |
| 3,858,577 | 1/1975 | Bass et al. ............................ | 606/15 |
| 3,906,953 | 9/1975 | Wallace et al. . | |
| 3,941,121 | 3/1976 | Olinger ............................... | 128/6 |
| 4,072,147 | 2/1978 | Hett . | |
| 4,120,293 | 10/1978 | Muckerheide . | |
| 4,146,019 | 3/1979 | Bass et al. . | |
| 4,172,451 | 10/1979 | Kline . | |
| 4,207,874 | 6/1980 | Choy . | |
| 4,240,441 | 12/1980 | Khalil . | |
| 4,266,548 | 5/1981 | Davi . | |
| 4,336,809 | 6/1982 | Clark . | |
| 4,341,221 | 7/1982 | Testerman . | |
| 4,369,794 | 1/1983 | Furler . | |
| 4,461,283 | 7/1984 | Doi . | |
| 4,469,098 | 9/1984 | Davi . | |
| 4,500,855 | 2/1985 | Feinberg ............................. | 307/425 |
| 4,522,212 | 6/1985 | Gelinas et al. . | |
| 4,559,951 | 12/1985 | Dahl et al. . | |
| 4,573,473 | 3/1986 | Hess . | |
| 4,576,177 | 3/1986 | Webster, Jr. . | |
| 4,587,972 | 5/1986 | Morantte, Jr. . | |
| 4,601,294 | 7/1986 | Danby et al. . | |
| 4,607,621 | 8/1986 | Wheeler ............................... | 128/6 |
| 4,641,650 | 2/1987 | Mok ..................................... | 606/15 |
| 4,641,912 | 2/1987 | Goldenberg ........................ | 606/15 |
| 4,669,467 | 6/1987 | Willett et al. . | |
| 4,672,961 | 6/1987 | Davies . | |
| 4,681,104 | 7/1987 | Edelman . | |
| 4,685,458 | 8/1987 | Leckrone . | |
| 4,690,152 | 9/1987 | Juncosa . | |
| 4,692,148 | 9/1987 | Kantrowitz et al. . | |
| 4,699,147 | 10/1987 | Chilson et al. . | |
| 4,785,815 | 11/1988 | Cohen ................................. | 128/642 |

Primary Examiner—Kyle L. Howell
Assistant Examiner—John C. Hanley
Attorney, Agent, or Firm—Wood, Herron & Evans

[57] ABSTRACT

An apparatus for detecting and treating abnormal electrical conducting tissue of an organ of the body which comprises a catheter insertable within a blood vessel or body cavity into proximity with the organ to be treated. An electrode or other electrical field-producing element is carried within the catheter and is effective to produce an electric field capable of inducing abnormal movement of the organ, e.g., a cardiac arrhythmia, when the electrode is placed at or near the focus of the abnormal electrical conducting tissue of the organ. A relatively undistorted image of such abnormal tissue is obtained using optical phase conjugation of a low energy laser beam which is directed to the focus of the damaged tissue and the along one or more optic fibers carried within the catheter to a viewing apparatus. A laser beam transmitted through another optic fiber carried within the catheter is then employed, if necessary, to destroy the damaged tissue.

18 Claims, 2 Drawing Sheets

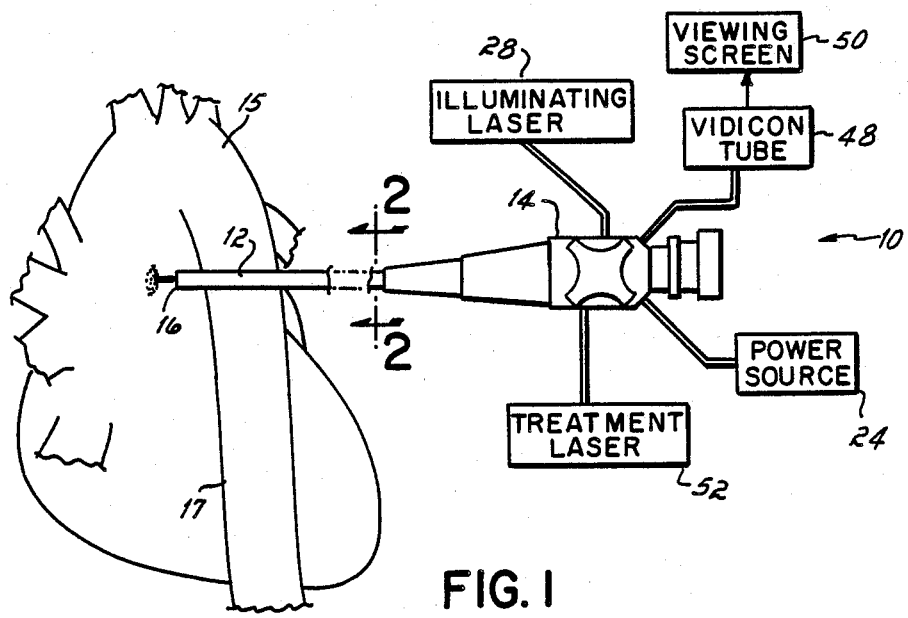
FIG. 1
FIG. 1A
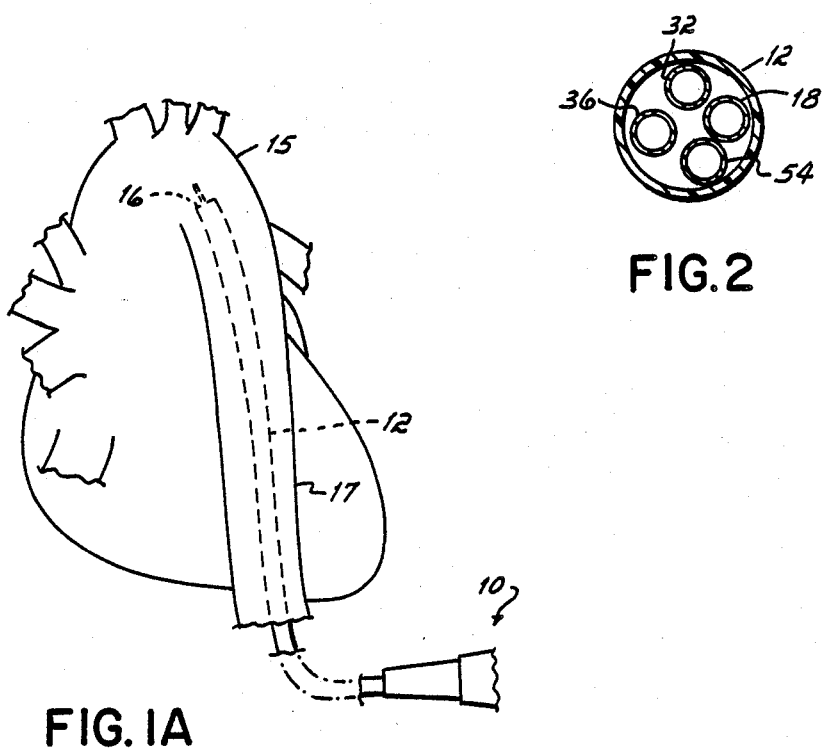
FIG. 2

LASER DIAGNOSTIC AND TREATMENT DEVICE

FIELD OF THE INVENTION

This invention relates to in vivo catheters or probes, and, more particularly, to an in vivo catheter capable of detecting abnormalities in the electrical conducting bundles of the heart or other electrical field-producing organs of the human body, and then treating the affected area with a laser.

BACKGROUND OF THE INVENTION

Many organs of the human body contain electrical conducting bundles which transmit electrical impulses to induce movement of the muscles of the organ. The electrical conducting bundles of the heart, for example, carry the electrical stimulus which induces rhythmic beating.

A heart attack can damage one or more portions of the electrical conducting bundles which stimulate heartbeats. The damaged or abnormal portion of the conducting bundle disturbs or interferes with the path of the electrical stimulus which induces the muscles of the heart to beat rhythmically. As a result of this disturbance of the electrical stimulus, the muscles of the heart can be induced to produce abnormal beating or arrhythmia which can be fatal.

Cardiac arrhythmia has been successfully treated with medication in some cases, but when that treatment is ineffective, open heart surgery is usually required. In an open heart surgical procedure, an attempt is made to remove the diseased or damaged electrical conducting bundles so that the electrical stimulus for the heart muscle can pass through unobstructed, healthy tissue. Often, a heart attack results in the damage of only a relatively small portion of the electrical conducting tissue, but a much larger area of tissue is removed during surgery. This is primarily due to the inability of current diagnostic techniques to precisely locate the diseased or damaged area of the heart. As a precaution, it has therefore been the practice for surgeons to remove more tissue than is really necessary in order to ensure that only healthy tissue remains.

Prior art apparatus and treatment methods have been proposed to improve current techniques of locating the damaged electrical conducting bundles of various organs, and to treat the damaged area without surgery. For example, a substantial effort has been made in the prior art to develop devices which are capable of more accurately diagnosing abnormalities in electrical field-producing organs, such as the heart, in which the apparatus senses the electrical field produced by the organ and emits signals for analysis by mapping instrumentation. Diagnostic apparatus of this general type are disclosed in U.S. Pat. Nos. 4,522,212; 4,559,951; 4,601,294; 4,341,221; 4,240,441; 4,172,451; 3,313,293; 4,369,794; 4,573,473; 4,692,148; 4,699,147; and, 4,690,152.

A great deal of research and development has also taken place to develop apparatus which avoid invasive surgical procedures such as open heart surgery. A number of apparatus have been designed which employ in vivo catheters or probes insertable through various blood vessels having lasers capable of destroying abnormalities associated with the heart or other organs such as arteriosclerotic plaque deposits and the like. Representative patents which disclose these types of devices include U.S. Pat. Nos. 4,685,458; 4,681,104; 4,672,961; 3,804,095; 4,461,283; 4,469,098; 4,207,874; 4,266,548; 4,336,809; 4,120,293; 3,659,613; 3,906,953; 4,072,147; and, 4,685,458.

One limitation of both the diagnostic devices and laser treatment devices disclosed in the patents listed above is that none incorporate both a sensing or diagnostic capability, and a laser treatment capability. The apparatus for diagnosing abnormalities in electrical field-producing organs have no means to treat the abnormality once it is discovered and located. On the other hand, the laser treatment devices disclosed in the patents listed above have no diagnostic capability. It is difficult to use one device to locate an abnormality in an organ, remove that device and then position a second, treatment device at the precise location of the damaged area of the organ identified by the diagnostic device.

This problem has been recognized in the apparatus disclosed, for example, in U.S. Pat. Nos. 4,576,177 and 4,587,972. Apparatus of this general type comprise an in vivo catheter having one optic fiber for transmitting laser irradiation and an ultrasonic transducer mounted at the tip of the catheter which transmits and receives ultrasonic signals. The catheter is inserted within a blood vessel, for example, and the ultrasonic transducer at the tip of the catheter is activated to transmit ultrasonic pulses through the catheter and against an obstruction such as arteriosclerotic plaque deposits. The ultrasonic echoes from the obstruction are received by the catheter and transmitted back to instrumentation located exteriorly of the patient which identifies or maps the obstruction. A laser beam is then transmitted through the optical fiber to destroy the obstruction while the catheter remains in place at the site of the obstruction.

Another type of apparatus found in the prior art having both a sensing and treatment capability is disclosed, for example, in U.S. Pat. Nos. 4,146,019; 4,207,874; and, 4,669,467. These patents generally disclose a catheter or probe having a pair of optical fibers for transmitting and receiving light to illuminate the obstruction. One of the optic fibers transmits laser light to the obstruction and the second optic fiber receives the reflected light which is transmitted back to a viewer. Once the obstruction is illuminated, the treatment laser is activated to destroy the obstruction.

While apparatus employing ultrasonic pulses or illumination are capable of permitting the attending physician to "view" an area of an organ or blood vessel, both provide relatively distorted maps or pictures of the affected area. This is because the ultrasonic pulses or laser light must pass through the fluids in the body cavity or vessel within which the catheter is inserted, both in moving to the affected area and in reflecting back from the affected area, and such fluids distort the image reproduced for viewing. In addition, such ultrasonic pulses or laser light are unable to penetrate, for example, the endocarcium and epicardium of the heart, which creates further distortion of the image of the underlying tissue. The applicability of such devices for the treatment of abnormalities other than the removal of arteriosclerotic plaque and the like is therefore limited.

SUMMARY OF THE INVENTION

It is therefore among the objectives of this invention to provide a method and apparatus for the treatment of abnormal or damaged electrical conducting tissue in an organ of the body such as the heart, which is capable of accurately locating the affected area, which does not require invasive surgery, which is effective to remove only the damaged or diseased area of the organ and which has a combined diagnostic and treatment capability.

These objectives are accomplished in the probe or catheter of this invention which comprises an outer tube carrying a number of optic fibers. One of the optic fibers houses an electrode connected to a low voltage source of electricity which produces an electric stimulus effective to induce a mild, abnormal movement of the organ to be treated, such as the heart, when the electrode is placed in the area of the organ having damaged or abnormal electrical conducting tissue. At least two other optic fibers are employed to carry low energy laser light for diagnostic purposes. The laser light is transmitted by one optic fiber to that area of the organ which has reacted abnormally to the electrical stimulus from the electrode, and then the laser light is reflected from the organ into the second optic fiber. Optical phase conjugation of this reflected beam received by the second optic fiber is employed to produce a conjugated beam which is transmitted in the reverse direction through the second optic fiber to the organ along the same path of transmission as the original reflected beam. The phase conjugated beam is reflected off of the organ and this reflected, conjugated beam travels back through the first optic fiber to a screen for viewing. Once the diseased or damaged area of the organ is located and identified by the aforementioned procedure, it is destroyed by a laser beam transmitted through a fourth optic fiber carried within the tube of the catheter.

This invention is predicated upon the provision of a catheter having an effective, combined diagnostic and treatment capability. The optic fiber carrying the electrode or other source of electrical stimulus provides a probe current which induces an abnormal movement of an organ when moved into proximity with any diseased or damaged electrically conductive bundles of the organ. The affected area is further defined and identified with the laser light-carrying optic fiber pair and optical phase conjugation techniques which produce a much clearer and less distorted image of the damaged area of the organ than can be obtained with conventional illumination or ultrasonic devices. If necessary, the laser treatment beam is then employed with the catheter in situ to destroy the abnormal or damaged tissue.

The catheter of this invention is useful in the diagnosis and treatment of abnormal tissue located either in the interior or exterior of an organ. In treating the heart, for example, the catheter is insertable through one or more of the vessels to the heart, or to the pericardium. In either case, the optical phase conjugation techniques employed in this invention produce a clearer image of the organ through the non-uniform distorting media in which the laser beams travel. The incident or mapping beam, and the phase conjugated beam, are both effective to penetrate the endocardium or epicardium of the heart and produce a relatively clear image of the tissue beneath.

In a presently preferred embodiment for treating the heart, for example, a low energy laser beam is transmitted from a controller at one end of the catheter into an optic fiber having a discharge end at the opposite end of the catheter. This laser, mapping beam penetrates the endocardium or epicardium of the heart and is reflected from the underlying tissue into a second optic fiber carried by the catheter. This reflected beam is transmitted by the second optic fiber to a photosensitive electro-optical optical phase conjugator located at the controller which includes an optical phase conjugation mirror and a monocrystal cut from a thermoconductive, electro-optic material such as BSO ($Bi_{12}SiO_{20}$). The optical phase conjugation mirror of the phase conjugator is effective to conjugate the reflected beam and send a phase conjugate beam in the reverse direction, and along the same exact path as the reflected beam, through the second optic fiber back to the heart. This phase conjugated beam again penetrates the endocardium or epicardium and is reflected from the damaged tissue of the heart back through the first optic fiber along substantially the same path as the mapping beam which it previously transmitted. The reflected, phase conjugate beam enters the controller of the catheter and is transmitted to the entry face of a vidicon through a lens. An image of the damaged tissue is then displayed on the screen for viewing.

Unlike viewing apparatus employed in the prior art, the optical phase conjugation techniques of this invention produce high quality optic beams through the non-uniform distorting media at the interior or exterior of a body organ. A much more accurate and detailed image of the affected area is produced which enables more precise analysis and identification of the damaged electrical transmission bundles in the tissue of the organ. Once such area is identified, a treatment laser beam transmitted through a fourth optic fiber carried in the catheter can be appropriately positioned and activated, if necessary, to destroy only that portion of the organ having the abnormal electrically conductive bundle.

DESCRIPTION OF THE DRAWINGS

The structure, operation and advantages of the presently preferred embodiment of this invention will become further apparent from the following description taken in conjunction with the accompanying drawings, wherein:

FIG. 1 is a schematic perspective view of the laser diagnostic and treatment catheter of this invention in position for the external treatment of a heart;

FIG. 1A is a view similar to FIG. 1 with the catheter of this invention positioned for the internal treatment of the heart;

FIG. 2 is a cross sectional view of the tube of the catheter herein illustrating the relative positioning of the optic fibers.

DETAILED DESCRIPTION OF THE INVENTION

Figure 3:
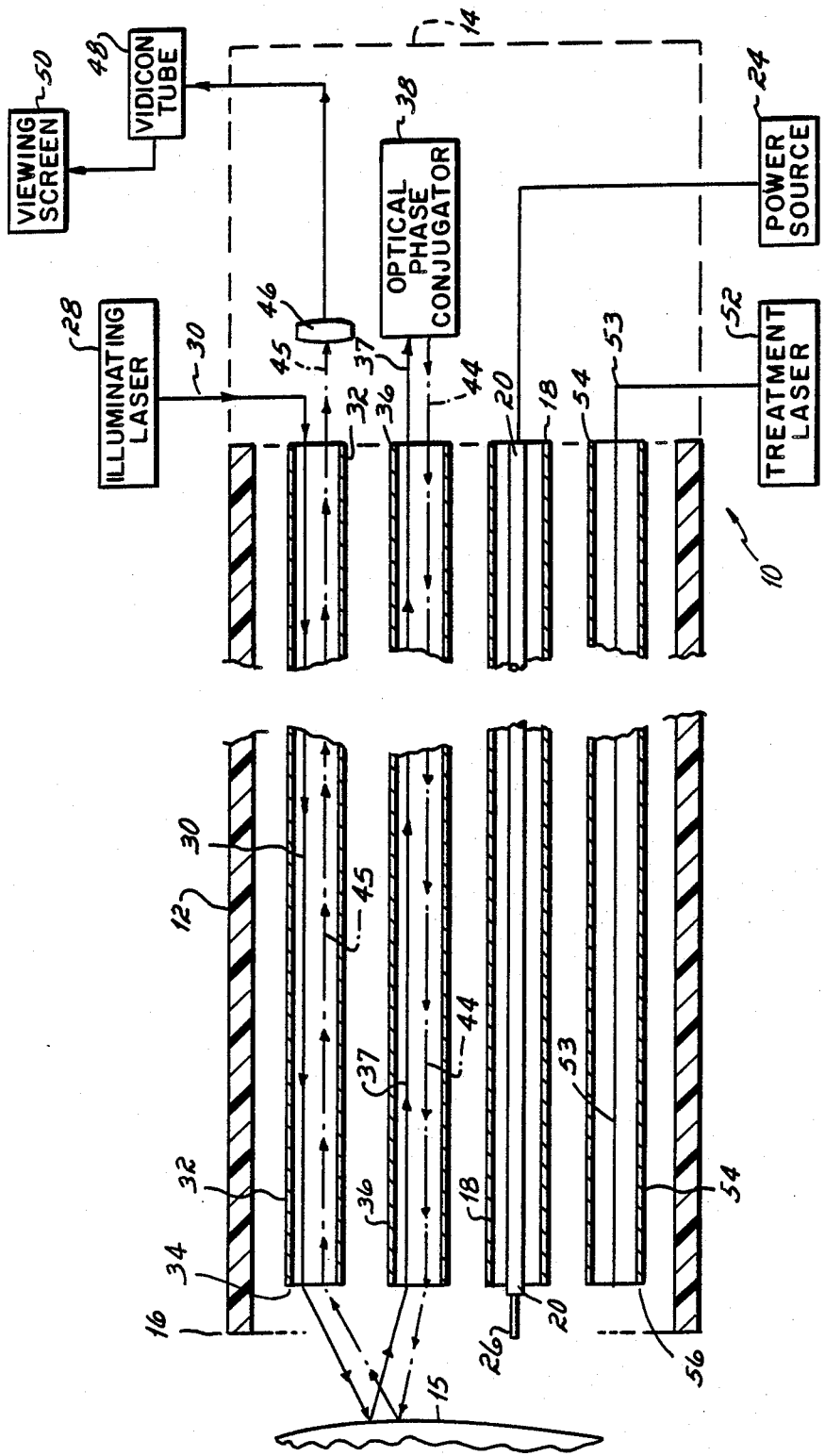
FIG. 3 is an enlarged, schematic view of the catheter and the controller illustrating the optical phase conjugation elements of this invention.

Referring now to the Figs., the laser treatment and diagnostic catheter 10 comprises a hollow, flexible tube 12 having a control unit 14 mounted at one end and a tip 16 at the opposite end. The flexible tube 12 carries at least four optic fibers which extend between the control unit 14 and tip 16. These optic fibers are held in fixed position within the tube 12 at relative locations such as illustrated in FIG. 2.

As illustrated in FIGS. 1 and 2, the flexible tube 12 of catheter 14 is capable of both internal and external treatment of an affected organ such as a heart 15. The flexible tube 12 is insertable through a vessel 17 into the interior of the heart as viewed in FIG. 1A, or, alternatively, the flexible tube 12 can be directed to the pericardium at any point along the outside of the heart 15. See FIG. 1. In both cases, the procedure for locating the catheter 10 of this invention is relatively non-invasive and in that respect is preferable to alternative prior art methods of treatment such as open heart surgery.

Referring now to FIGS. 1 and 3, a first optic fiber 18 carries a wire or electrode 20 coated with a dielectric material which is connected by a coupling at the control unit 14 to a low voltage, low current source of electrical energy illustrated schematically as a power source and designated with the reference number 24 in FIG. 1. The electrode 20 terminates at the tip 16 of the flexible tube 12 with an exposed end 26 which extends slightly forwardly of the tip 16. The electrode 20 is effective to transmit a low voltage, low amperage electrical probe current therethrough which is discharged from its exposed end 26 in the vicinity of the endocardium or epicardium of the heart 15 as schematically illustrated in FIGS. 1 and 1A. This probe current is sufficient to create a small arrhythmia in the heart 15 when the electrode 20 is placed in the vicinity of the focus of an abnormal, electrically conductive bundle (not shown) thereof.

Once the focus of an abnormal or damaged area of the heart 15 has been identified by the electrode 20 in this manner, a second diagnostic portion of the catheter 10 is effective to further define and identify the damaged area of heart 15. This second diagnostic portion of catheter 10 employs optical phase conjugation techniques to produce a relatively undistorted image or map of the damaged area of the heart 15 for subsequent laser treatment or scanning. Reference should be made to the text *Optical Phase Conjugation*, Robert A. Fisher, Academic Press, 1983, for a detailed discussion of optical phase conjugation and exemplary systems employing such technique, the disclosure of which is incorporated by reference in its entirety herein.

For purposes of describing the instant invention, the optical phase conjugation elements of this invention are schematically illustrated in FIG. 3. The control unit 14 is connected to a low power, illuminating laser 28 which transmits a mapping, laser beam 30 into an optic fiber 32 carried within the flexible tube 12 having a discharge end 34 at the tip 16 of the flexible tube 12. The mapping beam 30 strikes the heart 15 and at least a portion of the mapping beam 30 forms a reflected beam 37. This reflected beam 37 is transmitted through a third optic fiber 36 mounted within the flexible tube 12 between the tip 16 and the control unit 14.

A photosensitive, electro-optical optical phase conjugator 38 is carried within the control unit 14 in a position to receive the reflected beam 37 traveling through the third optic fiber 36. The optical phase conjugator 38 includes an optical phase conjugation mirror and a monocrystal (not shown). The monocrystal is preferably cut from a thermoconductive, electro-optical material such as BSO ($Bi_{12}SiO_{20}$). The reflected beam 37 is conjugated by the optical phase conjugator 38 producing an optical phase conjugated beam 44 which is transmitted in the opposite direction through the third optic fiber 36 to the heart 15. The phase conjugated beam 44 and reflected beam 37 within optic fiber 36 are shown as being spaced from one another in FIG. 3 for illustration purposes, but it should be understood that the phase conjugated beam 44 is transmitted in the reverse direction along substantially the identical path as the reflected beam 37.

The conjugated beam 44 is then reflected off of the heart 15 and at least a portion thereof enters the optic fiber 32 producing a reflected, phase conjugated beam 45. This reflected, phase conjugated beam 45 moves through the optic fiber 32 in the opposite direction from the initial, mapping beam 30, i.e., toward the control unit 14, and along substantially the same path as the mapping beam 30. The reflected, phase conjugated beam 45 enters the control unit 14 from the optic fiber 32 and is transmitted through a lens 46 to the entrance face of a vidicon 48 located exteriorly of the control unit 14. This image can then be displayed on a screen 50, also located exteriorly of the control unit 14, for viewing by the attending physician.

The optical phase conjugator 38 is capable of substantially reducing the distortion of the laser image of the heart 15 in a manner explained in detail in the text *Optical Phase Conjugation* referenced above. The mapping beam 30 and the phase conjugated beam 44 are both effective to penetrate the endocardium or epicardium of the heart 15 so that an image of the underlying tissue is provided. This substantially reduces the distortion obtained by prior art techniques which are not capable of penetrating these thin membranes of the heart 15.

The catheter 10 of this invention therefore provides the attending physician first with an indication of the location of the focus of a damaged or abnormal electrical conducting bundle of the heart 15 by operation of the electrode 20, and then a relatively undistorted and accurately representative image of the affected area is provided using optical phase conjugation techniques. At this point, the affected area or bundle of the heart 15 can be treated, i.e., destroyed, by the operation of a treatment laser 52 connected to the control unit 14 of catheter 10.

In the presently preferred embodiment, the treatment laser 52 may be an argon, copper vapor, gold vapor, holmium, flashed pump dye, carbon dioxide, erbium or a similar laser source. A laser beam 53 is transmitted from the treatment laser 52 through the control unit 14 into a fourth optic fiber 54 carried within the flexible tube 12 of catheter 10. This fourth optic fiber 54 has a discharge end 56 located at the tip 16 of tube 12 which is oriented to direct the beam from laser 52 at the damaged electrical conducting bundle of heart 15 to destroy it. Having removed the abnormal tissue or bundle, the surrounding, healthy tissue of the heart 15 is effective to transmit uninterrupted electrical stimulus to the muscles of the organ to induce rhythmic movement and avoid arrhythmia.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

For example, it is contemplated that the optical phase conjugation elements discussed above could be modified, or alternative elements employed, and still obtain the desired result of producing high quality optical beams for viewing. As described, two optical fibers 32 and 36 are utilized to transmit the mapping beam 30, reflected beam 37, phase conjugate beam 44 and reflected phase conjugate beam 45. Alternative embodiments might be employed wherein additional optic fibers are utilized to transmit one or more of these beams 30, 37, 44 or 45.

Therefore, it is intended that the invention not be limited to the particular embodiment disclosed as the best mode contemplated for carrying out this invention, but that the invention will include all embodiments falling within the scope of the appended claims.

We claim:

1. Apparatus for scanning organs of the body having abnormal, electrical conducting tissue, comprising:
   an optical imaginary catheter tube means adapted to be inserted in vivo in proximity to the abnormal, electrical conducting tissue of a body organ;
   optical phase conjugation means associated with said tube for producing a relatively undistorted image of said abnormal, electrical conducting tissue for viewing.

2. The apparatus of claim 1 in which said optical phase conjugation means comprises:
   first and second optic fibers carried within said tube means;
   said first optic fiber being aligned with a source of laser energy which produces a mapping beam, said mapping beam being directed in a first direction through said first optic fiber to said abnormal, electrical conducting tissue, said mapping beam being reflected in a second, reverse direction from said abnormal, electrical conducting tissue into said second optic fiber;
   an optical phase conjugator positioned with respect to said second optic fiber to receive said mapping beam reflected from said abnormal, electrical conducting tissue, said optical phase conjugator being effective to produce a phase conjugate beam which is directed in said first direction through said second optic fiber to said abnormal, electrical conducting tissue, said phase conjugate beam being reflected from said abnormal, electrical conducting tissue and being directed in said second direction into said first optic fiber;
   means for receiving said reflected, phase conjugate beam from said first optic fiber and producing an image of said abnormal, electrical conducting tissue.

3. Apparatus for detecting and diagnosing abnormal, electrical conducting tissue of an organ of the body, comprising:
   a tube adapted to be inserted in vivo in proximity to the abnormal, electrical conducting tissue of an organ of the body;
   electrode means carried within said tube for creating an electrical field, said electrical field being effective to induce abnormal movement of the organ upon placement of said electrode means into the vicinity of said abnormal, electrical conducting tissue of the organ;
   optical phase conjugation means associated with said tube for producing a phase conjugate beam which carries a relatively undistorted image of said abnormal, electrical conducting tissue for viewing.

4. The apparatus of claim 3 in which said electrode means comprises an electrode carried within an optic fiber located in said tube, said electrode being effective to create an electric field in the vicinity of the organ to be treated.

5. The apparatus of claim 3 in which said optical phase conjugation means comprises:
   first and second optic fibers carried within said tube;
   said first optic fiber being aligned with a a source of laser energy which produces a mapping beam, said mapping beam being directed in a first direction through said first optic fiber to said abnormal, electrical conducting tissue, said mapping beam being reflected in a second, reverse direction from said abnormal, electrical conducting tissue into said second optic fiber;
   an optical phase conjugator positioned with respect to said second optic fiber to receive said mapping beam reflected from said abnormal, electrical conducting tissue, said optical phase conjugator being effective to produce a phase conjugate beam which is directed in said first direction through said second optic fiber to said abnormal, electrical conducting tissue, said phase conjugate beam being reflected from said abnormal, electrical conducting tissue and being directed in said second direction into said first optic fiber;
   means for receiving said reflected, phase conjugate beam from said first optic fiber and producing an image of said abnormal, electrical conducting tissue.

6. Apparatus for treating organs of the body having abnormal, electrical conducting tissue, comprising:
   a tube adapted to be inserted in vivo in proximity to the abnormal, electrical conducting tissue of a body organ;
   optical phase conjugation means associated with said tube for producing a phase conjugate beam which carries a relatively undistorted image of said abnormal, electrical conducting tissue for viewing;
   laser means for transmitting a laser beam through said tube and into contact with said abnormal, electrical conducting tissue to destroy said tissue.

7. The apparatus of claim 6 in which said optical phase conjugation means comprises:
   first and second optic fibers carried within said tube;
   said first optic fiber being aligned with a source of laser energy which produces a mapping beam, said mapping beam being directed in a first direction through said first optic fiber to said abnormal, electrical conducting tissue, said mapping beam being reflected in a second, reverse direction from said abnormal, electrical conducting tissue into said second optic fiber;
   an optical phase conjugator positioned with respect to said second optic fiber to receive said mapping beam reflected from said abnormal, electrical conducting tissue, said optical phase conjugator being effective to produce a phase conjugate beam which is directed in said first direction through said second optic fiber to said abnormal, electrical conducting tissue, said phase conjugate beam being reflected from said abnormal, electrical conducting tissue and being directed in said second direction into said first optic fiber;
   means for receiving said reflected, phase conjugate beam from said first optic fiber and producing an image of said abnormal, electrical conducting tissue.

8. The apparatus of claim 6 in which said laser means comprises a laser source chosen from the group of argon, copper vapor, gold vapor, holmium, flash pumped dye, erbium and carbon dioxide.

9. Apparatus for detecting and treating abnormal, electrical conducting tissue of an organ of the body, comprising:

a tube adapted to be inserted in vivo in proximity to the abnormal, electrical conducting tissue of an organ of the body;

electrode means carried within said tube for creating an electrical field, said electrical field being effective to induce abnormal movement of the organ upon placement of said electrode means into the vicinity of said abnormal, electrical conducting tissue of the organ;

optical phase conjugation means associated with said tube for producing a phase conjugate beam which carries a relatively undistorted image of said abnormal, electrical conducting tissue for viewing;

laser means for transmitting a laser beam through said tube and into contact with said abnormal, electrical conducting tissue to destroy said tissue.

10. The apparatus of claim 9 in which said electrode means comprises an electrode carried within an optic fiber located in said tube, said electrode being effective to create an electric field in the vicinity of the organ to be treated.

11. The apparatus of claim 9 in which said optical phase conjugation means comprises:

first and second optic fibers carried within said tube;

said first optic fiber being aligned with a a source of laser energy which produces a mapping beam, said mapping beam being directed in a first direction through said first optic fiber to said abnormal, electrical conducting tissue, said mapping beam being reflected in a second, reverse direction from said abnormal, electrical conducting tissue into said second optic fiber;

an optical phase conjugator positioned with respect to said second optic fiber to receive said mapping beam reflected from said abnormal, electrical conducting tissue, said optical phase conjugator being effective to produce a phase conjugate beam which is directed in said first direction through said second optic fiber to said abnormal, electrical conducting tissue, said phase conjugate beam being reflected from said abnormal, electrical conducting tissue and being directed in said second direction into said first optic fiber;

means for receiving said reflected, phase conjugate beam from said first optic fiber and producing an image of said abnormal, electrical conducting tissue.

12. Apparatus for detecting and treating abnormal, electrical conducting tissue of an organ of the body, comprising:

a hollow tube having an inlet end and a discharge end, said hollow tube being adapted to be inserted in vivo so that said discharge end can be located in the vicinity of abnormal, electrical conducting tissue of an organ;

a first optic fiber carried within said tube, said first optic fiber supporting an electrode connected to an electrical power source, said electrode having an exposed end at said discharge end of said tube which creates an electrical field adjacent to the organ, said electrical field being effective to induce abnormal movement of the organ upon placement of said discharge end of said electrode into the vicinity of the abnormal, electrical conducting tissue;

second and third optic fibers carried within said tube;

said second optic fiber being aligned with a source of a laser energy which produces a mapping beam, said mapping beam being directed in a first direction through said second optic fiber to said abnormal, electrical conducting tissue, said mapping beam being reflected from said abnormal, electrical conducting tissue in a second direction into said third optic fiber;

an optical phase conjugator positioned with respect to said third optic fiber to receive said mapping beam reflected from said abnormal, electrical conducting tissue, said phase conjugator being effective to produce a phase conjugate beam which is directed in said first direction through said third optic fiber to said abnormal, electrical conducting tissue, said phase conjugate beam being reflected from said abnormal, electrical conducting tissue and being directed in said second direction into said second optic fiber;

means for receiving said reflected, phase conjugate beam from said second optic fiber and producing an image of said abnormal, electrical conducting tissue;

a fourth optic fiber carried within said tube;

treatment laser means operatively connected to said fourth optic fiber for transmitting a treatment laser beam therethrough and into contact with the abnormal, electrical conducting tissue to destroy said tissue.

13. The method of scanning abnormal, electrical conducting tissue of a body organ in vivo, comprising:

directing an illuminating beam onto said area of abnormal, electrical conducting tissue to form a reflected beam;

employing optical phase conjugation to form a relatively undistorted image of said abnormal, electrical conducting tissue from said reflected beam for viewing.

14. The method of detecting and diagnosing abnormal, electrical conducting tissue of a body organ, comprising:

producing an electric field in the vicinity of an area of abnormal, electrical conducting tissue of an organ of the body to induce abnormal movement of the organ;

directing an illuminating beam onto said area of abnormal, electrical conducting tissue to form a reflected beam;

employing optical phase conjugation to form a relatively undistorted image of said abnormal, electrical conducting tissue from said reflected beam for viewing.

15. The method of scanning abnormal, electrical conducting tissue of a body organ, comprising:

directing a laser beam onto the area of abnormal, electrical conducting tissue of an organ to form a reflected beam;

directing said reflected beam to an optical phase conjugator to produce a phase conjugated beam;

directing said phase conjugated beam to said area of abnormal, electrical conducting tissue to form a reflected, phase conjugate beam;

directing said reflected, phase conjugate beam to viewing means for producing an image of said area of abnormal, electrical conducting tissue for viewing.

16. The method of detecting and diagnosing abnormal, electrical conducting tissue of a body organ, comprising:

producing an electric field in the vicinity of an area of abnormal, electrical conducting tissue of an organ of the body to induce abnormal movement of the organ;

directing a laser beam onto said area of abnormal, electrical conducting tissue to form a reflected beam;

directing said reflected beam to an optical phase conjugator to produce a phase conjugated beam;

directing said phase conjugated beam to said area of abnormal, electrical conducting tissue to form a reflected, phase conjugate beam;

directing said reflected, phase conjugate beam to viewing means for producing an image of said area of abnormal, electrical conducting tissue.

17. The method of detecting and treating abnormal, electrical conducting tissue of a body organ, comprising:

producing an electric field in the vicinity of an area of abnormal, electrical conducting tissue of an organ of the body to induce abnormal movement of the organ;

directing an illuminating beam onto said area of abnormal, electrical conducting tissue to form a reflected beam;

employing optical phase conjugation to form a relatively undistorted image of said abnormal, electrical conducting tissue from said reflected beam;

directing a treatment laser beam to said abnormal, electrical conducting tissue to destroy said tissue.

18. The method of detecting and treating abnormal, electrical conducting tissue of a body organ, comprising:

producing an electric field in the vicinity of an area of abnormal, electrical conducting tissue of an organ of the body to induce abnormal movement of the organ;

directing an illuminating beam onto said area of abnormal, electrical conducting tissue to form a reflected beam;

directing said reflected beam to an optical phase conjugator to produce a phase conjugate beam;

directing said phase conjugate beam to said area of abnormal, electrical conducting tissue to form a reflected, phase conjugate beam;

directing said reflected, phase conjugate beam to viewing means for producing an image of said area of abnormal, electrical conducting tissue;

directing a laser beam to said abnormal, electrical conducting tissue to destroy said tissue.

* * * * *